United States Patent [19]

Mayer

[11] Patent Number: 6,152,900

[45] Date of Patent: *Nov. 28, 2000

[54] NEEDLELESS INJECTION SITE

[75] Inventor: Bruno Franz P. Mayer, Santa Ana, Calif.

[73] Assignee: Becton, Dickinson and Company, Franklin Lakes, N.J.

[*] Notice: This patent is subject to a terminal disclaimer.

[21] Appl. No.: 09/186,222

[22] Filed: Nov. 4, 1998

Related U.S. Application Data

[63] Continuation of application No. 09/035,227, Mar. 5, 1998, which is a continuation of application No. 08/699,848, Aug. 20, 1996, Pat. No. 5,820,601, which is a continuation-in-part of application No. 08/493,744, Jun. 22, 1995, Pat. No. 5,616,130, which is a continuation-in-part of application No. 08/401,854, Mar. 10, 1995, Pat. No. 5,616,129, which is a continuation-in-part of application No. 08/262,994, Jun. 20, 1994, Pat. No. 5,470,319.

[51] Int. Cl.⁷ .......................... A61M 5/00; A61M 5/178
[52] U.S. Cl. ..................... 604/167; 604/256; 251/149.1
[58] Field of Search ............................ 604/167, 256, 604/249, 245, 246, 283, 414, 905; 251/149.1, 149.6, 149.2

[56] References Cited

U.S. PATENT DOCUMENTS

| | | | |
|---|---|---|---|
| 3,977,555 | 8/1976 | Larson | 215/247 |
| 4,063,460 | 12/1977 | Svensson | 73/425.6 |
| 4,134,512 | 1/1979 | Nugent | 215/247 |
| 4,246,899 | 1/1981 | Loseff | 128/276 |
| 4,301,936 | 11/1981 | Percarpio | 215/247 |
| 4,338,764 | 7/1982 | Percarpio | 53/432 |
| 4,655,752 | 4/1987 | Honkanen et al. | 604/256 |
| 4,838,855 | 6/1989 | Lynn | 604/49 |
| 4,874,377 | 10/1989 | Newgard et al. | 604/167 |
| 5,064,416 | 11/1991 | Newgard et al. | 604/167 |
| 5,100,394 | 3/1992 | Dudar et al. | 604/283 |
| 5,122,123 | 6/1992 | Vaillancourt | 604/192 |
| 5,122,129 | 6/1992 | Olson et al. | 604/905 |
| 5,135,489 | 8/1992 | Jepson et al. | 604/48 |

(List continued on next page.)

FOREIGN PATENT DOCUMENTS

| | | |
|---|---|---|
| 2001732 | 4/1990 | Canada . |
| 0309771A1 | 4/1989 | European Pat. Off. . |
| 0544581A1 | 11/1991 | European Pat. Off. . |
| 3105437A1 | 10/1982 | Germany . |
| 93/05838 | 4/1993 | WIPO . |
| 93/05839 | 4/1993 | WIPO . |
| 93/11828 | 6/1993 | WIPO . |
| 9600107 | 6/1994 | WIPO . |
| 97/21464 | 6/1997 | WIPO . |

*Primary Examiner*—John G. Weiss
*Assistant Examiner*—David J. Cho
*Attorney, Agent, or Firm*—Eric M. Lee, Esq.

[57] ABSTRACT

A needleless injection site comprising a housing which defines an interior chamber and a central opening which communicates with the interior chamber. The housing further comprises an elongate, proximally extending dilator projection portion which defines a fluid passage. Disposed within the central opening and the interior chamber is a reseal member which has an elastically openable and closable aperture disposed therein and defines an expandable and collapsible internal reservoir. The reseal member normally resides in a first position within the housing wherein the aperture is in a closed configuration and the reservoir is collapsed. The reseal member is deformable such that the application of distally directed pressure thereto will cause the reseal member to distally advance within the housing to a second position wherein the aperture assumes an open configuration and communicates with the fluid passage and the reservoir. The cessation of the application of distally directed pressure to the reseal member will cause it to resiliently return to the first position wherein the aperture reassumes the closed configuration and the reservoir is collapsed. The collapse of the reservoir is adapted to prevent the creation of a vacuum within the fluid passage when the reseal member resiliently returns to its first position.

14 Claims, 2 Drawing Sheets

U.S. PATENT DOCUMENTS

| | | | |
|---|---|---|---|
| 5,154,703 | 10/1992 | Bonaldo | 604/244 |
| 5,158,554 | 10/1992 | Jepson et al. | 604/283 |
| 5,171,234 | 12/1992 | Jepson et al. | 604/283 |
| 5,188,620 | 2/1993 | Jepson et al. | 604/283 |
| 5,201,725 | 4/1993 | Kling | 604/284 |
| 5,203,775 | 4/1993 | Frank et al. | 604/256 |
| 5,207,661 | 5/1993 | Repschlager | 604/317 |
| 5,215,538 | 6/1993 | Larkin | 604/249 |
| 5,234,413 | 8/1993 | Wonder et al. | 604/248 |
| 5,242,425 | 9/1993 | White et al. | 604/256 |
| 5,242,432 | 9/1993 | Defrank | 604/284 |
| 5,250,033 | 10/1993 | Evans et al. | 604/160 |
| 5,269,771 | 12/1993 | Thomas et al. | 604/213 |
| 5,273,533 | 12/1993 | Bonaldo | 604/83 |
| 5,286,453 | 2/1994 | Pope | 422/100 |
| 5,324,256 | 6/1994 | Lynn et al. | 604/49 |
| 5,336,192 | 8/1994 | Palestrant | 604/167 |
| 5,360,012 | 11/1994 | Ebara et al. | 128/764 |
| 5,360,413 | 11/1994 | Leason et al. | 604/249 |
| 5,380,306 | 1/1995 | Brinon | 604/244 |
| 5,401,245 | 3/1995 | Haining | 604/86 |
| 5,439,451 | 8/1995 | Collinson et al. | 604/247 |
| 5,470,319 | 11/1995 | Mayer | 604/167 |
| 5,474,544 | 12/1995 | Lynn | 604/283 |
| 5,487,728 | 1/1996 | Vaillancourt | 604/86 |
| 5,501,426 | 3/1996 | Atkinson et al. | 251/149.1 |
| 5,509,912 | 4/1996 | Vaillancourt et al. | 604/283 |
| 5,514,116 | 5/1996 | Vaillancourt et al. | 604/283 |
| 5,520,665 | 5/1996 | Fleetwood | 604/283 |
| 5,520,666 | 5/1996 | Choudhury et al. | 604/283 |
| 5,549,566 | 8/1996 | Elias et al. | 604/167 |
| 5,549,577 | 8/1996 | Siegel et al. | 604/256 |
| 5,578,059 | 11/1996 | Patzer | 604/249 |
| 5,616,129 | 4/1997 | Mayer | 604/167 |
| 5,616,130 | 4/1997 | Mayer | 604/167 |
| 5,620,434 | 4/1997 | Brony | 604/406 |
| 5,669,891 | 9/1997 | Vaillancourt | 604/283 |
| 5,685,866 | 11/1997 | Lopez | 604/249 |
| 5,688,254 | 11/1997 | Lopez et al. | 604/283 |
| 5,690,612 | 11/1997 | Lopez et al. | 604/93 |
| 5,694,686 | 12/1997 | Lopez | 29/890.126 |
| 5,695,466 | 12/1997 | Lopez et al. | 604/93 |
| 5,699,821 | 12/1997 | Paradis | 137/1 |
| 5,700,248 | 12/1997 | Lopez | 604/249 |
| 5,820,601 | 10/1998 | Mayer | 604/167 |

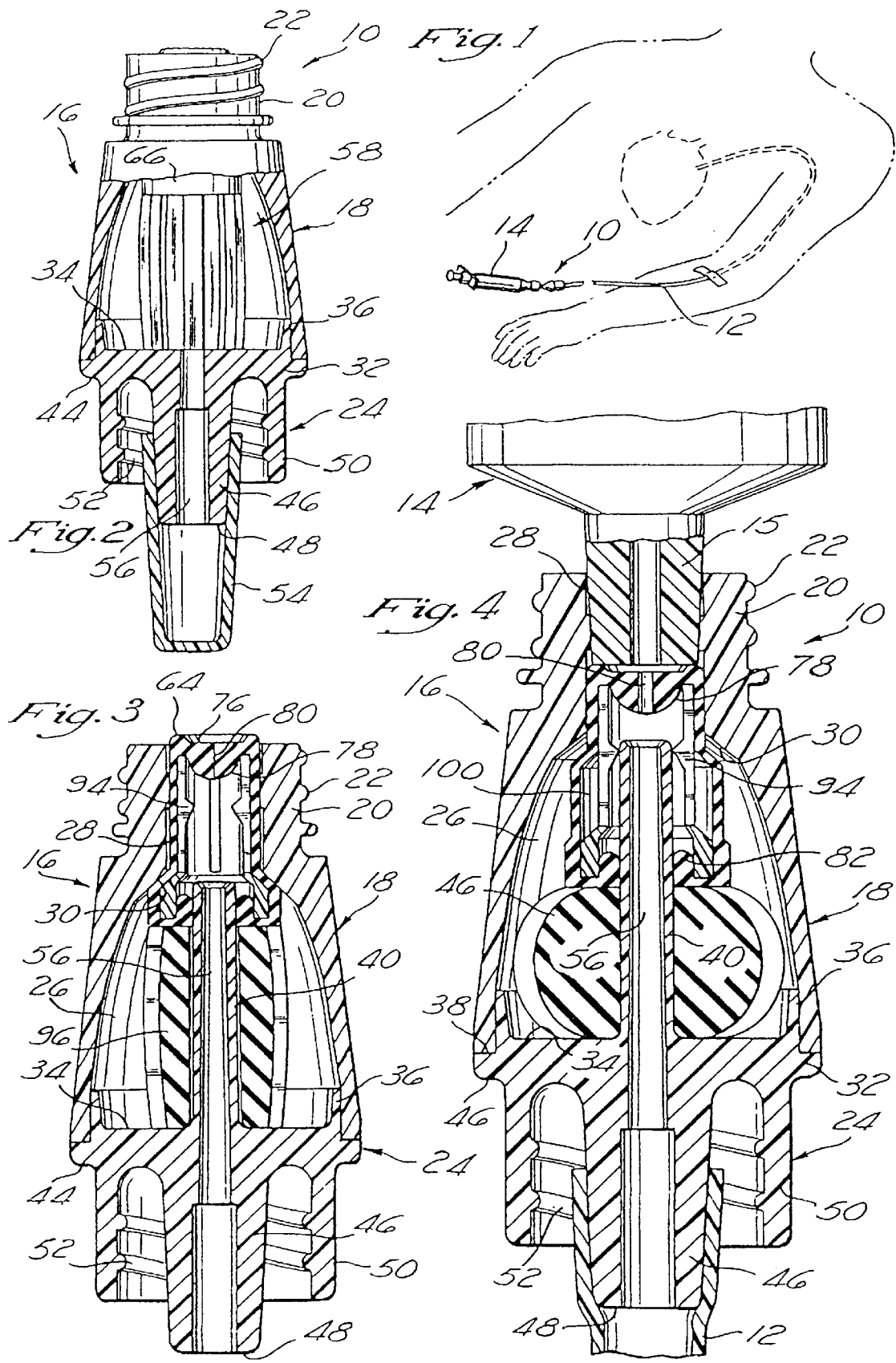

NEEDLELESS INJECTION SITE

RELATED APPLICATIONS

The present application is a continuation of U.S. application Ser. No. 09/035,227 entitled NEEDLELESS INJECTION SITE filed Mar. 5, 1998, which is a continuation of U.S. application Ser. No. 08/699,848 entitled NEEDLELESS INJECTION SITE filed Aug. 20, 1996 and now U.S. Pat. No. 5,820,601 issued Oct. 13, 1998, which is a continuation-in-part of U.S. application Ser. No. 08/493,744 entitled NEEDLELESS INJECTION SITE filed Jun. 22, 1995 and now U.S. Pat. No. 5,616,130 issued Apr. 1, 1997, which is a continuation-in-part of U.S. application Ser. No. 08/401,854 entitled NEEDLELESS INJECTION SITE filed Mar. 10, 1995 and now U.S. Pat. No. 5,616,129 issued Apr. 1, 1997, which is a continuation-in-part of U.S. application Ser. No. 08/262,994 entitled NEEDLELESS INJECTION SITE filed Jun. 20, 1994 and now U.S. Pat. No. 5,470,319 issued Nov. 28, 1995.

FIELD OF THE INVENTION

BACKGROUND OF THE INVENTION

It is common medical practice to intravenously infuse various fluids or medicaments into a blood vessel of a patient (e.g., a vein or artery). Such infusion is typically accomplished by the insertion of a hollow introducer needle into a target blood vessel. The introducer needle is fluidly connected to one end of an elongate, flexible tube or fluid line, the opposite end of which is fluidly connected to a solution bag. The solution bag itself is typically suspended above the patient so as to allow gravity to facilitate the flow of fluid downwardly through the fluid line and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment and introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of the conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks.

In recognition of this deficiency, there has also been developed in the prior art needleless injection sites which incorporate a diaphragm adapted to assume open and closed configurations without having a needle inserted thereinto. Though these needleless injection sites eliminate the necessity of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting agent thereto. However, due to the configuration of the diaphragm, complete and effective disinfection thereof is often difficult to achieve, thus increasing the risk of the inadvertent introduction of contaminates into the solution stream upon subsequent uses of the injection site.

In an effort to overcome the deficiencies associated with the prior art injection sites, Applicant developed the needleless injection sites disclosed in the previously identified issued patent and co-pending applications which are the parents of the present application. The present needleless injection site constitutes an improvement over that disclosed in U.S. Pat. No. 5,470,319 in that the same is adapted to accommodate needled introducers as well as non-needled introducers in the event the infusion of medication into the injection site must be accomplished in a short time during an emergency situation through the use of a needled introducer. Additionally, the needleless injection site constructed in accordance with the present application constitutes an improvement over those disclosed in U.S. application Ser. Nos. 08/401,854 and 08/493,744 in that the same is specifically configured so as not to pull a vacuum within the tubular fluid line connected thereto when a needled or non-needled introducer is withdrawn from therewithin.

SUMMARY OF THE INVENTION

In accordance with the present invention, there is provided a needleless injection site comprising a housing which defines an interior chamber and a central opening which communicates with the interior chamber. Preferably formed on the outer surface of the housing about the central opening thereof are Luer threads. The housing further defines an elongate, proximally extending dilator projection portion which extends toward and is co-axially aligned with the central opening. In addition to the dilator projection portion, the housing defines an elongate, distally extending adaptor portion which extends away from the central opening. The dilator projection and adaptor portions collectively define a continuous fluid passage.

In addition to the housing, the needleless injection site of the present invention comprises a reseal member which is disposed within the central opening and the interior chamber of the housing. The reseal member includes an elastically openable and closable aperture disposed therein, and defines an expandable and collapsible internal reservoir. The reseal member normally resides in a first position within the housing wherein the aperture is in a closed configuration and the reservoir is collapsed. The reseal member is selectively deformable such that the application of distally directed pressure thereto will cause the same to distally advance within the housing to a second position wherein the reservoir is expanded and the aperture assumes an open configuration and communicates with the fluid passage and the reservoir. The removal of the distally directed pressure from the reseal member facilitates the resilient return thereof to the first position wherein the aperture reassumes the closed configuration and the reservoir is collapsed. Importantly, the collapse of the reservoir is adapted to prevent the creation of a vacuum within the fluid passage when the reseal member resiliently returns to its first position.

In the preferred embodiment, the reseal member comprises a resilient body which includes a distal end, a proximal end having inner and outer surfaces, and an aperture extending between the inner and outer surfaces of the proximal end. The proximal end is defined by a generally cylindrical proximal portion of the body, with the distal end being defined by a generally cylindrical distal portion of the body having a diameter exceeding that of the proximal portion. Formed between the proximal and distal portions of the body is a generally cylindrical middle portion having a diameter which exceeds that of the proximal portion, but is less than the diameter of the distal portion. The transition between the middle portion and the proximal and distal portions is defined by a pair of beveled shoulders. The inner surface of the proximal end of the body preferably has a generally semi-spherical configuration, with the aperture extending axially between the outer surface of the proximal end and the apex of its semi-spherical inner surface.

Disposed within the body is a radial leaf spring which includes a plurality of leaf portions having elongate slots extending therebetween. The leaf portions are adapted to apply a radially inward biasing force to the proximal end of the body which maintains the aperture in the closed configuration when no distally directed pressure is applied to the outer surface of the proximal end. The reservoir of the reseal member is defined between the radial leaf spring and the body, with the slots defining fluid flow channels between the aperture and the reservoir when the reseal member is moved to its second position, and between the reservoir and the fluid passage during the return of the reseal member to its first position.

The reseal member further comprises an elongate, generally cylindrical donut spring having a first end which is abutted against the distal end of the body, a second end, and a bore extending longitudinally therethrough. In the preferred embodiment, the donut spring has a splined configuration, and includes elongate channels extending longitudinally within the outer surface thereof. When the reseal member is in its first position, a beveled shoulder of the body and the second end of the donut spring are abutted against the housing. In this respect, the donut spring is preferably sized such that a slight compression force (i.e., a pre-load) is applied thereto when the reseal member is in its first position. Both the body and the donut spring of the reseal member are preferably fabricated from silicone, though similar alternative materials may also be employed in the injection site of the present invention.

In the preferred embodiment, the dilator projection portion of the housing extends into the reseal member, and more particularly is extended through the bore of the donut spring and into the radial leaf spring. In this respect, the body further defines an annular flange which extends radially inward from the distal end thereof and is abutted against the dilator projection portion of the housing when the same is extended through the bore and into the reseal member, thus creating a fluid-tight seal therebetween. The application of distally directed pressure to the outer surface of the proximal end of the body causes the radial leaf spring to be distally advanced over the dilator projection portion. The resultant outward flexion of the leaf portions facilitates the radial expansion of the aperture to its open configuration. Such outward flexion of the leaf portions is assisted by ramp portions formed on the inner surfaces thereof which engage the dilator projection portion as the reseal member is distally advanced thereover. Additionally, the movement of the reseal member toward its second position facilitates the expansion of the reservoir from its normally collapsed state.

Conversely, the removal of the distally directed pressure from the outer surface of the proximal end causes the radial leaf spring to be proximally withdrawn from over the dilator projection portion. Such proximal movement facilitates the resilient return of the aperture to its closed configuration, and the compression of the reservoir. When the reseal member is moved to its second position, the donut spring is compressed between the distal end of the body and the housing. As such, the movement of the reseal member back to its first position is facilitated by the resilient return of the donut spring to its normal, slightly compressed configuration.

Importantly, when the reseal member is distally advanced to its second position, intravenous fluid introduced thereinto via the open aperture flows into the expanded reservoir via the slots defined between the radial leaf portions of the radial leaf spring. In addition to flowing into the reservoir, such fluid flows directly into the fluid passage. When the reseal member resiliently returns to its first position, the resultant collapse of the reservoir forces the fluid from therewithin back through the slots defined between the radial leaf portions and into the fluid passage, thus creating a zero or positive displacement therewithin, i.e., preventing a vacuum from being created within the fluid passage. In the preferred embodiment, the reservoir is sized to displace approximately 0.035 ml of retained fluid volume. In this respect, the volumetric capacity of the reservoir is preferably equal to or greater than the inner diameter of the fluid passage multiplied by the axial travel distance of the reseal member when the same moves from its first position to its second position.

In the preferred embodiment, the housing comprises an upper section which defines the central opening, and a lower section which is attached to the upper section. When attached to each other, the upper and lower sections collectively define the interior chamber. The lower section itself preferably comprises a central portion which is attached to the upper section via a sonic weld, and includes the dilator projection portion extending proximally from one side thereof and the adaptor portion extending distally from the opposite side thereof. The adaptor portion of the lower section preferably comprises a tubing connection having a tapered outer surface and a blunt distal tip. Slidably extensible over and frictionally maintainable upon the tubing connection is a breather cap. The lower section further includes a distal lock region which circumvents the adaptor portion and preferably includes a plurality of Luer threads formed therewithin.

BRIEF DESCRIPTION OF THE DRAWINGS

These, as well as other features of the present invention, will become more apparent upon reference to the drawings wherein:

FIG. 1 is a perspective view illustrating an exemplary manner in which the needleless injection site constructed in accordance with the present invention is used to facilitate fluid infusion into an anatomical passage;

FIG. 2 is a partial cross-sectional view of the needleless injection site constructed in accordance with the present invention;

FIG. 3 is a cross-sectional view of the needleless injection site shown in FIG. 2, illustrating the reseal member thereof in a first, closed position;

FIG. 4 is a cross-sectional view of the reseal member shown in FIG. 2, illustrating the reseal member thereof as deformed into a second, open position.

DETAILED DESCRIPTION OF THE PREFERRED EMBODIMENT

Figure 5:
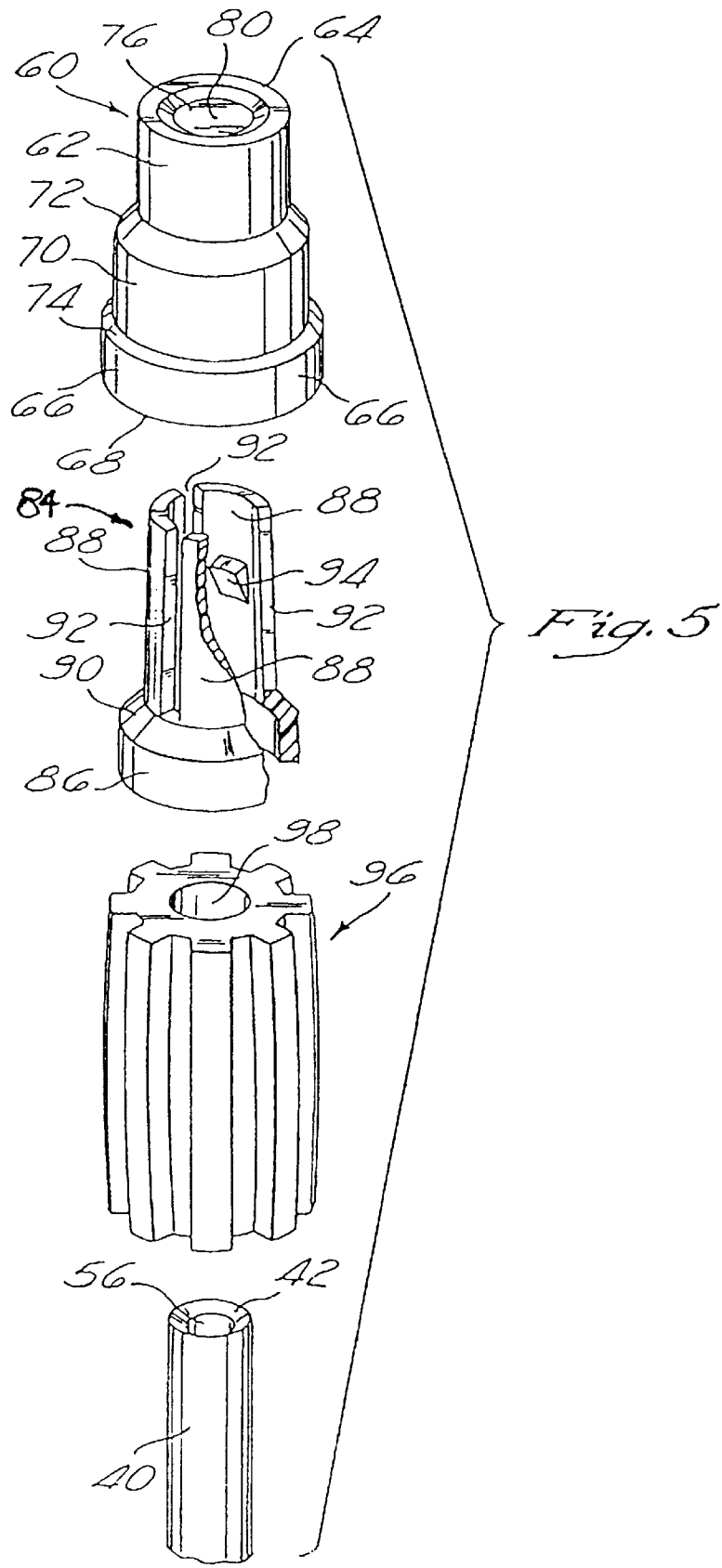
FIG. 5 is an exploded view illustrating the components comprising the reseal member shown in FIGS. 3 and 4.

Referring now to the drawings wherein the showings are for purposes of illustrating a preferred embodiment of the present invention only, and not for purposes of limiting the same, FIG. 1 illustrates the needleless injection site 10 constructed in accordance with the present invention as used to facilitate the infusion of a medicament into a blood vessel (e.g., a vein or artery) of a patient. As will be discussed in more detail below, the needleless injection site 10 of the present invention presents advantages over those constructed in accordance with the prior art in that the same is specifically adapted to create a zero or positive displacement of fluid within the fluid line 12 extending from the injection site 10 to the blood vessel of the patient when a non-needled introducer 14 is withdrawn from therewithin. Importantly, such zero or positive displacement of fluid prevents a vacuum from being created within the fluid line 12, thus eliminating any back-flow of blood thereinto. As will be recognized, any back-flow of blood into the fluid line 12 is highly undesirable, in that the coagulation thereof may obstruct the fluid line 12 or create a clot which inadvertently passes into the blood vessel of the patient.

Referring now to FIGS. 2–5, the injection site 10 of the present invention comprises a hollow housing 16. The housing 16 itself comprises an upper section 18 which defines a reduced diameter proximal portion 20 having Luer threads 22 formed on the outer surface thereof. In addition to the upper section 18, the housing 16 includes a lower section 24 which is rigidly attached to the upper section 18. When attached to each other, the upper and lower sections 18, 24 collectively define an interior chamber 26. In this respect, the proximal portion 20 of the upper section 18 defines a central opening 28 which communicates with the interior chamber 26. As best seen in FIGS. 3 and 4, the transition between the central opening 28 and interior chamber 26 is defined by an annular, inclined shoulder 30 formed within the inner surface of the upper section 18.

In the preferred embodiment, the lower section 24 includes a central portion 32 defining a generally planar, circularly configured proximal surface 34 which is circumvented by an annular flange portion 36. Formed within the outer surface of the central portion 32 and extending thereabout is a continuous, annular shoulder 38. When the upper and lower sections 18, 24 are attached to each other, the distal rim of the upper section 18 is abutted against the shoulder 38, with the flange portion 36 extending along the inner surface of the upper section 18 in direct contact therewith. The attachment of the upper and lower sections 18, 24 to each other is preferably facilitated by a sonic weld between the distal rim of the upper section 18 and the shoulder 38 defined by the lower section 24. However, it will be recognized by those of ordinary skill in the art that alternative attachment methods, such as the use of adhesives, may be employed in the injection site 10. The upper and lower sections 18, 24 are sized such that when rigidly attached to each other in the aforementioned manner, the outer surface of the upper section 18 is substantially flush with the outer surface of the central portion 32 of the lower section 24.

Extending proximally from the proximal surface 34 of the central portion 32 in substantially perpendicular relation thereto is an elongate dilator projection portion 40 which is coaxially aligned with the central opening 28 of the upper section 18. The dilator projection portion 40 has a generally cylindrical configuration, and defines a blunt proximal tip 42. In addition to the dilator projection portion 40, formed on the lower section 24 and extending distally from the distal surface 44 of the central portion 32 thereof is an elongate adaptor portion 46. In the injection site 10, the adaptor portion 46 preferably comprises a tubing connection which defines a tapered outer surface and a blunt distal tip 48. Also extending distally from the distal surface 44 of the central portion 32 is a distal lock region 50 which circumvents the adaptor portion 46 and is used to facilitate the connection of the housing 16 to an annular surface. In the preferred embodiment, the distal lock region 50 includes Luer threads 52 formed on its inner surface, and is sized such that the distal tip 48 of the adaptor portion 46 protrudes beyond the distal rim thereof.

As seen in FIG. 4, the adaptor portion 46 is configured to facilitate the connection of the injection site 10 to the fluid line 12. Such connection is achieved by the advancement of the adaptor portion 46 into one end of the lumen of the fluid line 12, with the adaptor portion 46 being sized and configured so as to be frictionally retained therewithin. It will be recognized that the distal lock region 50 may be used to connect the injection site 10 to infusion components other than for the fluid line 12. When the adaptor portion 46 is not being used to facilitate the connection of the injection site 10 to the fluid line 12 or other infusion components, the same is typically covered by a breather cap 54 which has a complementary configuration and is advanced thereover and frictionally maintained thereupon, as seen in FIG. 2. Importantly, the dilator projection and adaptor portions 40, 46 of the lower section 24 collectively define an elongate fluid passage 56 which extends through the lower section 24 and is co-axially aligned with the central opening 28 of the upper section 18.

Referring now to FIGS. 3–5, the injection site 10 constructed in accordance with the present invention further comprises a reseal member 58 which is disposed within the central opening 28 and interior chamber 26 of the housing 16. The reseal member 58 comprises a resilient body 60 having a generally cylindrical proximal portion 62 which defines a proximal end 64, and a generally cylindrical distal portion 66 which defines a distal end 68. Disposed between the proximal and distal portions 62, 66 is a cylindrically configured middle portion 70. The proximal, middle and distal portions 62, 70, 66 are of progressively increasing diameter, with the diameter of the distal portion 66 exceeding that of the middle portion 70, and the diameter of the middle portion 70 exceeding that of the proximal portion 72. The transition between the proximal and middle portions 62, 70 is defined by a first beveled shoulder 72, with the transition between the middle and distal portions 70, 66 being defined by a second beveled shoulder 74.

In the preferred embodiment, the proximal end 64 of the body 60 defines a recessed, circularly configured outer surface 76 which has a generally planar configuration. In addition to the outer surface 76, the proximal end 64 defines a generally semi-spherical inner surface 78. Extending axially through the proximal end 64 from the outer surface 76 to the apex of the inner surface 78 is an aperture 80. Additionally, formed about and extending radially inward from the distal end 68 of the body 60 is a continuous annular flange 82, the inner peripheral edge of which defines an enlarged bead. The body 60 is preferably fabricated from silicone, though the same may alternatively be fabricated from a similar resilient material such as rubber.

The reseal member further comprises a radial leaf spring 84 which is disposed within the body 60. The radial leaf spring 84 comprises a generally cylindrical base portion 86 which transitions into three (3) identically configured, equidistantly spaced leaf portions 88 via a beveled shoulder 90. The leaf portions 88 are separated from each other by three (3) longitudinally extending slots 92 which extend to the shoulder 90. Formed on the inner surfaces of respective ones of the leaf portions 88 are generally wedge-shaped ramps 94, the use of which will be discussed in more detail below.

As best seen in FIGS. 3 and 4, the radial leaf spring 84 is disposed within the body 60 in a manner wherein the outermost ends of the leaf portions 88 are received into an annular channel circumventing the semi-spherical inner surface 78 of the proximal end 64. Additionally, the distal portion 66 of the body 60 is wrapped about the base portion 86 of the radial leaf spring 84 such that the flange 82 and in particular its lead extends about the inner surface thereof. The radial leaf spring 84 is preferably fabricated from polysulfone or polycarbonate, though similar rigid materials with memory may be utilized as an alternative.

In addition to the body 60 and radial leaf spring 84, the reseal member 58 of the injection site 10 comprises an elongate, generally cylindrical axial donut spring 96 which has a splined outer surface and includes a bore 98 extending longitudinally (i.e., axially) therethrough. As will be discussed in more detail below, the donut spring 96 defines a first or proximal end which is normally abutted against the distal end 68 of the body 60, and a second or distal end which is normally abutted against the housing 16, and in particular the proximal surface 34 of the central portion 32 of the lower section 24. Like the body 60, the donut spring 96 is preferably fabricated from silicone, though the same may alternatively be fabricated from a similar resilient material such as rubber.

In the injection site 10, the aperture 80 extending through the proximal end 64 of the body 60 is elastically openable and closable. In this respect, the reseal member 58 of the injection site 10 normally resides in a first position within the housing 16 (shown in FIG. 3) wherein the aperture 80 is in a closed configuration. Importantly, the reseal member 58 is selectively deformable such that the application of distally directed pressure thereto, and in particular the raised lip circumventing the outer surface 76 of the proximal end 64,
will cause the same to distally advance within the housing 16 to a second position (shown in FIG. 4) wherein the aperture 80 assumes an open configuration. As will be discussed in more detail below, due to the resiliency of the reseal member 58, and in particular the donut spring 96 thereof, the removal of the distally directed pressure from the proximal end 64 will cause the reseal member 58 to resiliently return to its first position wherein the aperture 80 reassumes the closed configuration.

When the reseal member 58 is disposed in its normal, first position within the housing 16, the dilator projection portion 40 of the lower section 24 is extended through the bore 98 of the donut spring 96 and into the hollow interior of the radial leaf spring 84. In this respect, the proximal tip 42 of the dilator projection portion 40 extends to approximately the beveled shoulder 90 of the radial leaf spring 84. When extended into the radial leaf spring 84, the dilator projection portion 40 passes through the opening defined by the annular flange 82 of the body 60, and in particular the bead defined thereby. Importantly, the diameter of the opening defined by this bead is less than the outer diameter of the dilator projection portion 40. As such, when the dilator projection portion 40 passes through this opening, the bead is sealed in a fluid-tight manner against the outer surface thereof, i.e., the bead is compressed between the outer surface of the dilator projection portion 40 and the inner surface of the base portion 86 of the radial leaf spring 84.

Additionally, when the reseal member 58 is in its first position, both the proximal and middle portions 62, 70 of the body 60 reside within the central opening 28 of the upper section 18, with the second beveled shoulder 74 and distal portion 66 of the body 60, as well as the donut spring 96, residing within the interior chamber 26 of the housing 16. Importantly, though the diameter of the middle portion 70 of the body 60 exceeds the diameter of the proximal portion 62 thereof, both the proximal and middle portions 62, 70 extend along and cover the outer surfaces of the leaf portions 88 when the reseal member 58 is in its first position. In this respect, due to the middle portion 70 being disposed within the central opening 28, the same is collapsed (i.e., compressed) against the outer surfaces of the leaf portions 88, thereby "flattening" the first beveled shoulder 72 normally defined between the proximal and middle portions 62, 70. When the reseal member 58 is in its first position, the second beveled shoulder 74 of the body 64 extends along and covers the shoulder 90 of the radial leaf spring 84, and is compressed between the shoulder 90 and the inclined shoulder 30 formed in the inner surface of the upper section 18. Additionally, the proximal end 64 of the body 60 protrudes slightly beyond the rim of the proximal portion 20 of the upper section 18, as best seen in FIGS. 2 and 3.

As previously indicated, the proximal end of the donut spring 96 is abutted against the distal end 68 of the body 60, with the distal end of the donut spring 96 being abutted against the central portion 32 of the lower section 24, and in particular the proximal surface 34 thereof. Importantly, in the injection site 10, the distance separating the shoulder 30 from the proximal surface 34 of the central portion 32 is slightly less than the combined length of the distal portion 66 of the body 60 and donut spring 96. Thus, when the reseal member 58 is disposed in its first position within the housing 16, the donut spring 96 is slightly compressed between the distal end 68 of the body 60 and the proximal surface 34 of the central portion 32, thus applying a pre-load thereto which causes the same to bulge slightly outwardly as shown in FIG. 3. Due to the application of the pre-load thereto, the donut spring 96 is operable to force the middle portion 70 of the body 60 upwardly into the central opening 28, thus collapsing the same in the aforementioned manner and facilitating the compression of the second beveled shoulder 74 between the shoulders 30, 90. Importantly, when the reseal member 58 is in its first position, the leaf portions 88 of the radial leaf spring 84 apply a radially inward biasing force to the proximal end 64 of the body 60 which maintains the aperture 80 in its closed configuration.

As seen in FIG. 4, the application of distally directed pressure to the proximal end 64 of the body 60 by an infusion component such as the tip 15 of the introducer 14 causes the radial leaf spring 84 to be distally advanced over the dilator projection portion 40. Such advancement removes the second beveled shoulder 74 of the body 60 from its abutting contact with the shoulder 30, and further forces the middle portion 70 of the body 60 from within the central opening 28. Additionally, such distal advancement facilitates the compression of the donut spring 96, thus causing the same to bulge outwardly within the interior chamber 26 of the housing 16. Importantly, the camming action of the dilator projection portion 40 against the leaf portions 88, and in particular the ramps 94 formed on the inner surfaces thereof, causes the same to be flexed outwardly, thus facilitating the radial expansion of the aperture 80 to its open configuration.

Additionally, since the middle portion 70 of the body 60 is removed from within the constricting central opening 28 of the upper section 18, the same resiliently returns to its normal orientation (shown in FIG. 5), thereby forming the first beveled shoulder 72 and defining an expandable and collapsible reservoir 100 between the inner surface of the middle portion 70 and the outer surfaces of the leaf portions 88 and shoulder 90 of the radial leaf spring 84. Thus, when the reseal member 58 is moved to its second position as shown in FIG. 4, the proximal portion 62 of the body 60 extends along and covers the outer surfaces of the leaf portions 88, with the distal portion 66 extending along and covering the base portion 86 of the radial leaf spring 84. However, the middle portion 70 of the body 60 is spaced from the outer surfaces of the leaf portions 88, thus defining the reservoir 100. In this respect, only the proximal portion 62 of the body 60 resides within the central opening 28, with the middle and distal portions 70, 66 of the body 60 and the fully compressed donut spring 96 residing within the interior chamber 26.

When the reseal member 58 of the injection site 10 is moved to its second position as shown in FIG. 4, the open aperture 80 communicates with both the fluid passage 56 and the reservoir 100. In particular, the open aperture 80 is co-axially aligned with the fluid passage 56, thus creating a continuous flow path between the introducer 14, the fluid passage 56, and the infusion component (such as the fluid line 12) to which the adaptor portion 46 is connected. The open aperture 80 fluidly communicates with the reservoir 100 via the slots 92 extending between the leaf portions 88 of the radial leaf spring 84. As such, a medicament dispensed from the introducer 14 flows through the open aperture 80, and into the fluid passage 56 and reservoir 100. Importantly, the medicament expelled from the introducer 14 is prevented from leaking into the interior chamber 26 by the seal created by the abutment of the tip 15 of the introducer 14 against the raised lip circumventing the outer surface 76 of the proximal end 64, and by the seal created by the compression of the flange 82 between the dilator projection portion 40 and base portion 86 of the radial leaf spring 84. As will be recognized, the seal created by the flange 82 is a sliding seal which travels longitudinally along the dilator projection portion 40 as the reseal member 58 is advanced to its second position.

Due to the resiliency of the donut spring 96, the removal of the distally directed pressure from the proximal end 64 causes the radial leaf spring 84 to be proximally withdrawn from over the dilator projection portion 40, thus facilitating the resilient return of the reseal member 58 to its first position, as shown in FIG. 3. The return of the reseal member 58 to its first position causes the aperture 80 to resiliently return to its closed configuration. Additionally, as the reseal member 58 moves toward its first position, the resultant forcing of the middle portion 70 of the body 60 into the central opening 28 facilitates the collapse of the reservoir 100 since, as previously explained, the middle portion 70 is compressed against the outer surfaces of the leaf portions 88 when the reseal member 58 is in its first position. Importantly, this collapse of the reservoir 100 causes the fluid previously introduced thereinto to be expelled from therewithin and into the fluid passage 56 via the slots 92 extending between the leaf portions 88 of the radial leaf spring 84. The advantages attendant to this resultant flow of fluid into the fluid passage 56 during the return of the reseal member 58 to its first position will be discussed in more detail below.

As previously explained, in prior art needleless injection sites there is a tendency for blood to be drawn into the fluid line extending into the anatomical passage when the introducer is withdrawn from within the injection site. Such back-flow of blood is attributable to the vacuum created in the fluid line when the introducer is withdrawn from within the prior art injection site. Advantageously, the collapse of the reservoir 100 of the injection site 10 in the aforementioned manner prevents a vacuum from being created within the fluid line 12 when the reseal member 58 moves from its second position (shown in FIG. 4) to its first position (shown in FIG. 3). In this respect, the flow of fluid from the reservoir 100 into the fluid passage 56 creates zero or positive pressure within the fluid passage 56 and fluid line 12 coupled thereto, thus preventing blood from being drawn thereinto. Advantageously, the absence of blood within the fluid line 12 prevents any undesirable coagulation therewithin, and eliminates the risk of inadvertent obstruction of the fluid line 12.

In the preferred embodiment, the reservoir 100 is sized so as to displace a volume of fluid which is equal to or greater than the product of the mean internal diameter of the fluid passage 56 extending through the dilator projection portion 40 and the distance of axial travel of the reseal member 58 between its first and second positions. For most applications, the expanded reservoir 100 is sized having a volumetric capacity of approximately 0.035 ml which is sufficient to facilitate zero or positive pressure within the fluid passage 56 when the reseal member 58 is returned to its first position. It will be recognized that increasing the diameter of the middle portion 70 of the body 60 facilitates a resultant increase in the volumetric capacity of the reservoir 100. In this respect, an increase in the volume of the reservoir 100 causes positive pressure to be created within the fluid passage 56 when the reservoir 100 is collapsed. Conversely, the diameter of the middle portion 70 may be reduced such that the volume of the reservoir 100 causes zero pressure to be created in the fluid passage 56 when the reservoir 100 is collapsed. As previously explained, the injection site 10 shown in FIGS. 2–4, and in particular the housing 16 thereof, is adapted to be fluidly connected to the fluid line 12. Though not shown, it will be recognized that the housing 16 may be configured for connection to other infusion components as well. In this respect, other injection sites may be fabricated which include the reseal member 58 incorporated into a differently configured housing without departing from the spirit and scope of the present invention. Indeed, any housing with which the reseal member 58 is utilized need only be configured such that the reseal member 58 is movable between its first and second positions to create the fluid passage from the introducer 14 into the infusion component in the previously described manner.

Due to the configuration of the reseal member 58, in an emergency situation a medicament may be passed into the fluid passage 56 via a needled introducer device rather than through the non-needled introducer 14 previously described. In this respect, when a needled introducer device is utilized, the reseal member 58 will not be moved to its second position to facilitate the opening of the aperture 80. Rather, the needle of the needled introducer device is simply forced through the closed aperture 80 and into the fluid passage 56 of the dilator projection portion 40.

Additional modifications and improvements of the present invention may also be apparent to those skilled in the art. Thus, the particular combination of parts described and illustrated herein is intended to represent only one embodiment of the present invention, and is not intended to serve as limitations of alternative devices within the spirit and scope of the invention.

What is claimed is:

1. An injection site for controlling the flow of a fluid between an introducer and a fluid line, the injection site comprising:

a housing defining a flow passage which is placeable into communication with the introducer and the fluid line to permit fluid flow therebetween;

a reseal member disposed within the housing and movable between a first position whereat the flow passage is obstructed thereby and a second position whereat fluid is permitted to flow through the flow passage; and an expandable and contractible reservoir disposed within the housing and adapted to retain a volume of fluid when expanded;

the reseal member being cooperatively engaged to the housing such that the movement of the reseal member to the second position allows the reservoir to be filled with fluid, and the movement of the reseal member to the first position facilitates the contraction of the reservoir and the forcing of at least a portion of any fluid retained therein into the flow passage.

2. The injection site of claim 1 wherein:

the housing comprises an interior chamber and a central opening which communicates with the interior chamber and is sized to receive a portion of the introducer; and the reseal member is disposed within the central opening and the interior chamber.

3. The injection site of claim 2 wherein:

the reseal member includes an openable and closable aperture; and the reseal member is deformable such that the application of compressive pressure thereto via the insertion of the introducer into the central opening facilitates the movement thereof to the second position whereat the aperture is opened and the introducer is placed into communication with the flow passage and the reservoir, and the removal of the compressive pressure therefrom via the withdrawal of the introducer from within the central opening facilitates the resilient return thereof to the first position whereat the aperture is closed and the reservoir is contracted to force at least a portion of any fluid retained therein into the flow passage.

4. The injection site of claim 3 wherein the expandable and contractible reservoir is defined by the reseal member.

5. The injection site of claim 3 wherein:

the housing further comprises an elongate dilator projection portion which extends within the interior chamber and defines a fluid passage which forms a portion of the flow passage;

the movement of the reseal member to the second position facilitating the placement of the introducer into communication with the reservoir and the fluid passage, with the movement of the reseal member to the first position resulting in at least a portion of any fluid retained in the reservoir being forced into the fluid passage.

6. The injection site of claim 1 further comprising a spring member disposed within the housing and cooperatively engaged to the reseal member for normally biasing the reseal member to the first position.

7. The injection site of claim 1 wherein the reseal member is fabricated from silicone.

8. An injection site for controlling the flow of a fluid between an introducer and a fluid line, the injection site comprising:

a housing defining a flow passage which is placeable into communication with the introducer and the fluid line to permit fluid flow therebetween;

a reseal member disposed within the housing and movable between a first position whereat the flow passage is obstructed thereby and a second position whereat fluid is permitted to flow through the flow passage; and a reservoir disposed within the housing and adapted to retain a volume of fluid;

the reseal member being cooperatively engaged to the housing such that the movement of the reseal member to the second position allows the reservoir to be filled with fluid, and the movement of the reseal member to the first position results in at least a portion of any fluid retained within the reservoir being forced therefrom into the flow passage.

9. The injection site of claim 8 further comprising a spring member disposed within the housing and cooperatively engaged to the reseal member for normally biasing the reseal member to the first position.

10. The injection site of claim 8 wherein:

the housing comprises an interior chamber and a central opening which communicates with the interior chamber and is sized to receive a portion of the introducer; and the reseal member is disposed within the central opening and the interior chamber.

11. In an injection site having a housing which defines a flow passage placeable into communication with an introducer and a fluid line to permit fluid flow therebetween, a reseal member which is disposed within the housing and movable between a first position whereat the flow passage is obstructed thereby and a second position whereat fluid is permitted to flow through the flow passage, and a reservoir which is disposed within the housing and adapted to retain a volume of fluid, a method for preventing the creation of a vacuum within the flow passage and the fluid line upon disengagement of the introducer from the housing, the method comprising the steps of:

(a) causing the reservoir to be filled with a volume of fluid from the introducer upon the movement of the reseal member from the first position to the second position; and (b) forcing at least a portion of the volume of fluid retained within the reservoir into the flow passage and the fluid line upon the movement of the reseal member from the second position to the first position.

12. The method of claim 11 wherein:

step (a) comprises moving the reseal member from the first position to the second position by the application of compressive pressure thereto via the introducer; and step (b) comprises moving the reseal member from the second position to the first position by disengaging the introducer from the housing.

13. The method of claim 12 wherein the reseal member includes an openable and closable aperture, and:

step (a) comprises opening the aperture upon the movement of the reseal member to the second position so as to place the introducer into communication with the flow passage and the reservoir; and step (b) comprises closing the aperture upon the movement of the reseal member to the first position.

14. The method of claim 13 wherein the reservoir is expandable and contractible and adapted to retain the volume of fluid when expanded, and:

step (a) comprises expanding the reservoir upon the movement of the reseal member to the second position to allow the reservoir to be filled with the volume of fluid from the introducer; and step (b) comprises contracting the reservoir upon the movement of the reseal member to the first position to force at least a portion of the volume of fluid retained in the reservoir into the flow passage and the fluid line.

* * * * *